United States Patent [19]

Yen et al.

[11] 3,978,848

[45] Sept. 7, 1976

[54] MONITORING APPARATUS AND METHOD FOR BLOOD PRESSURE AND HEART RATE

[75] Inventors: David H. Yen, Sunnyvale; Tim R. Connelly, Campbell; John J. Lee, Sunnyvale, all of Calif.

[73] Assignee: Filac Corporation, Sunnyvale, Calif.

[22] Filed: Jan. 9, 1975

[21] Appl. No.: 539,799

[52] U.S. Cl. .................... 128/2.05 M; 128/2.05 T
[51] Int. Cl.² .......................................... A61B 5/02
[58] Field of Search ................ 128/2.05 A, 2.05 G, 128/2.05 M, 2.05 P, 2.05 T, 2.05 Z

[56] References Cited
UNITED STATES PATENTS

| | | | |
|---|---|---|---|
| 3,308,811 | 3/1967 | Gillette et al. ................ | 128/2.05 M |
| 3,405,707 | 10/1968 | Edwards ........................ | 128/2.05 M |
| 3,450,131 | 6/1969 | Vogt .............................. | 128/2.05 A |
| 3,533,401 | 10/1970 | Streu ............................. | 128/2.05 A |
| 3,552,383 | 1/1971 | Krueger et al. ................ | 128/2.05 A |
| 3,646,606 | 2/1972 | Buxton et al. ................. | 128/2.05 A |
| 3,779,235 | 12/1973 | Murphy, Jr. et al. ......... | 128/2.05 M |
| 3,814,083 | 6/1974 | Fletcher ........................ | 128/2.05 A |
| 3,841,314 | 10/1974 | Page .............................. | 128/2.05 A |

FOREIGN PATENTS OR APPLICATIONS

| | | | |
|---|---|---|---|
| 1,197,796 | 7/1970 | United Kingdom ............ | 128/2.05 A |

OTHER PUBLICATIONS

S.W. Institute of Elect. & Electronics Engnr. Conference Record, Apr., 1968, pp. 17F1–17F5.

Med. & Biol. Engineering, May, 1974, pp. 360–363.

Primary Examiner—Kyle L. Howell
Attorney, Agent, or Firm—Flehr, Hohbach, Test, Albritton & Herbert

[57] ABSTRACT

A combination blood pressure and heart rate monitor is disclosed of the type utilizing a pressure cuff coupled to a patient's artery. Acoustic means is provided and adapted to be placed in a transducing relationship to the artery for providing a sound signal. Pressure transducing means is provided responsive to the average pressure in the cuff and the heart rate pressure provided by the artery for providing an average pressure signal and a heart rate signal. Means is provided for detecting and comparing the sound signal and the heart rate signal for accurately determining, in combination with the average pressure, the patient's systolic and diastolic pressure levels.

6 Claims, 4 Drawing Figures

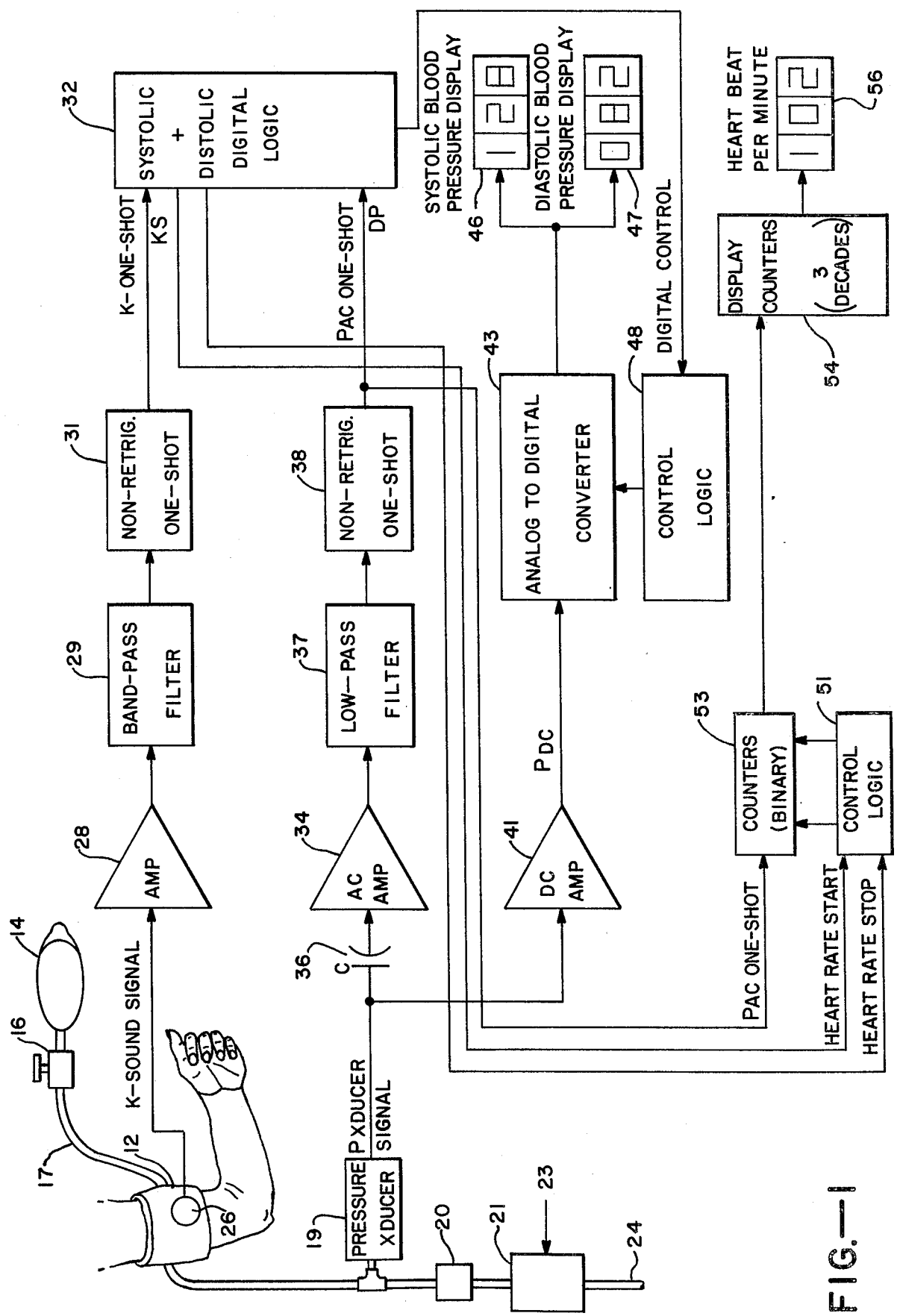
FIG.—1

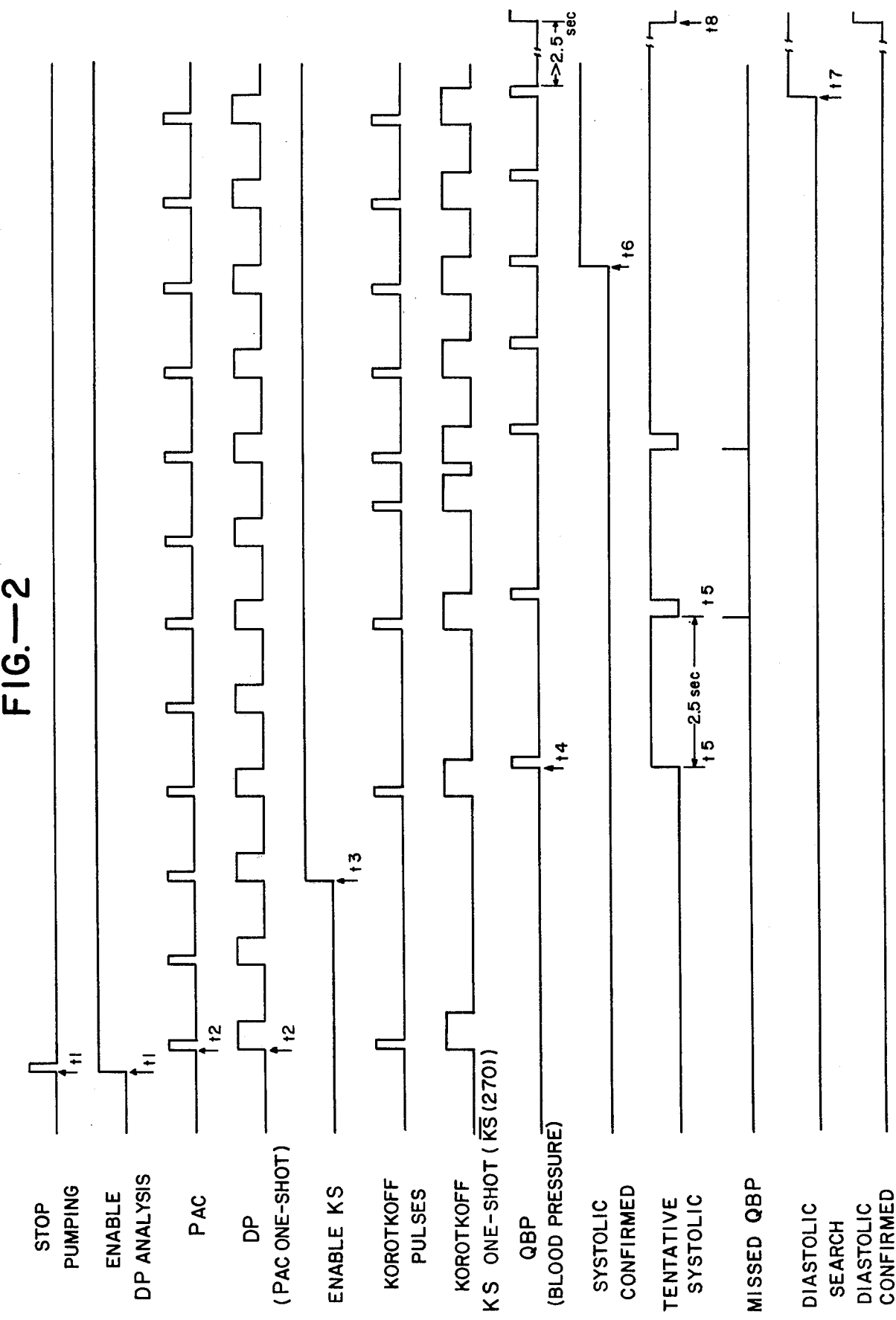

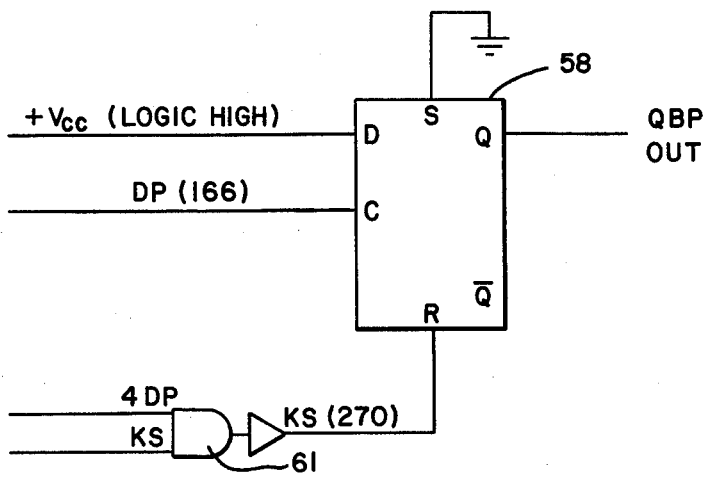
FIG.—3
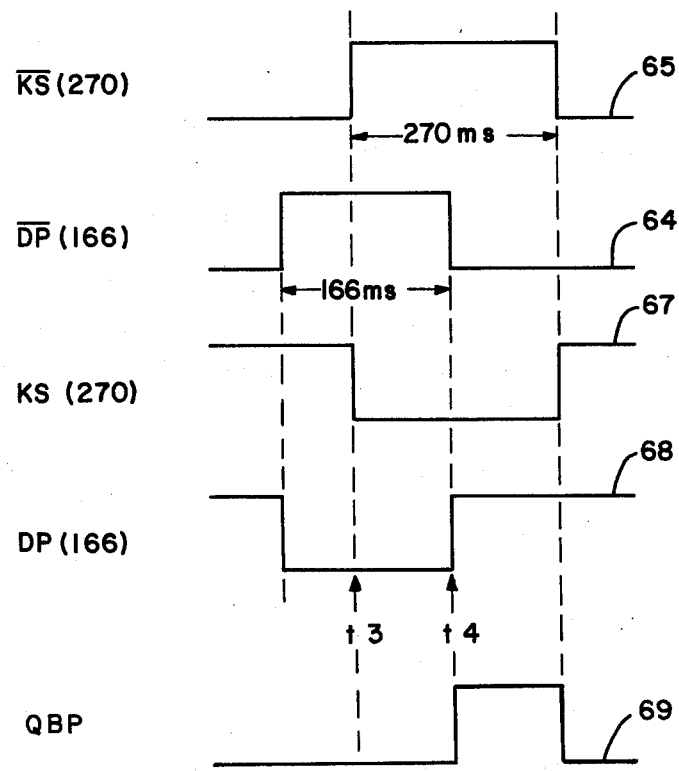
FIG.—4

MONITORING APPARATUS AND METHOD FOR BLOOD PRESSURE AND HEART RATE

BACKGROUND OF THE INVENTION

This invention relates generally to a measuring and monitoring apparatus for blood pressure and heart rate of a human patient. More particularly, this invention relates to an apparatus for determining a patient's blood pressure in accord with medically accepted pressure levels and heart rate measuring methods.

Although monitoring apparatus for blood pressure and heart rate have heretofore been provided, such apparatus have either required skilled personnel using a standard pressure cuff and stethoscope apparatus or alternately unskilled personnel utilizing complex apparatus which provides erroneous readings. Present equipment capable of being utilized by unskilled personnel suffers from erroneous readings due to artifact motion signals which may be contributed by noise associated with muscle movement, arm motor movement and general environmental noise. Thus there is a need for a monitoring apparatus capable of being operated by unskilled personnel which provides accurate blood pressure and heart rate readings.

OBJECTS AND SUMMARY OF THE INVENTION

Accordingly, it is a general object of the present invention to provide an improved monitoring apparatus for blood pressure and heart rate which may be operated by unskilled personnel.

It is a particular object of the present invention to provide an improved monitoring apparatus for rapidly and accurately measuring the blood pressure and heart rate.

The foregoing and other objects of the invention are achieved in a measurement method utilizing a monitoring apparatus for blood pressure and heart rate of the type employing a pressure cuff coupled to a patient's artery. The monitor includes acoustic means adapted to be placed in a transducing relationship to the artery for providing a sound signal. Pressure transducing means is provided and is responsive to the average pressure in the cuff and additionally the heart rate pressure provided by the artery. The pressure transducing means provides an average pressure signal and a heart rate signal. Means is provided for detecting and comparing the sound signal and the heart rate signal for accurately determining, in combination with the average pressure signal, the patient's systolic and diastolic pressure levels.

DESCRIPTION OF THE DRAWINGS

FIG. 1 is a symbolic block diagram of the present invention coupled to a patient's artery and providing blood pressure and heartbeat indications.

FIG. 2 is a timing diagram showing the operational sequence of the invention in performing measurements.

FIG. 3 is a detection circuit for use with the present invention.

FIG. 4 is a graphical representation of the FIG. 3 circuit.

DESCRIPTION OF THE PREFERRED EMBODIMENTS

The monitoring apparatus for measuring blood pressure and heart rate and the sequence of operations in carrying out measurement are shown in the accompanying Figures. As is appreciated in the art, the accepted clinical method for measuring blood pressure includes restricting arterial blood flow such as by a pressure cuff. The cuff is first inflated above the highest blood pressure anticipated, followed by stethoscope observation for Korotkoff sound signals produced as the cuff pressure is relieved. Korotkoff sounds are observed as a first audible pulse corresponding to a systolic pressure level, and with a continued decrease in cuff pressure, the disappearance of the audible sound at a second diastolic pressure level. Briefly, in general overview, the monitoring apparatus of the present invention obviates the need for skilled personnel to observe the Korotkoff sounds and by excluding noise and artifact motion signals permits accurate blood pressure determinations to be made by unskilled personnel employing the present invention.

Referring to FIG. 1, the monitoring apparatus for blood pressure and heart rate is shown. A pneumatic inflatable pressure cuff 12 is provided and is positioned by wrapping the cuff in a deflated state around the patient's upper arm. Cuff 12 is suitably positioned to restrict the brachial artery when the cuff is inflated. Cuff 12 may be inflated by fluid pressure means, such as a manual bulb 14 connected via valve 16 which is in fluid communication with cuff 12 by tube 17. A pressure transducer 19 and a solenoid release valve 21 are further connected in fluid communication with cuff 12. Solenoid 21 may provide, in response to a signal 23, a predetermined release of pressure in cuff 12 at outlet 24 in combination with needle valve 20. Acoustic transducing means 26, such as a microphone responsive to Korotkoff sounds, is adapted to be placed in a transducing relationship to the artery for providing a sound signal. Microphone 26 may be interposed within cuff 12 or positioned in a pocket formed in cuff 12 so as to form a single assembly which may be readily affixed or removed to facilitate rapid blood pressure and heart rate measurements. A Korotkoff sound amplifier 28 is provided having its input connected to the output of microphone 26. A bandpass filter 29 is provided having an input connected to the output of amplifier 28. Amplifier 28 having sufficient and suitable gain provides, in combination with bandpass filter 29, characteristics adjusted to pass the Korotkoff sound frequency range conventionally observed by a stethoscope. Filter 29 may provide an 18Hz. to 70Hz., 3db passband. Bandpass filter 29 has an output connected to the input of decision means 31 such as a non-retriggerable one-shot. The one-shot may have a period of approximately 270 milliseconds. The output of decision means 31 is connected to a first, KS input of digital logic block 32. Block 32 provides suitable systolic and diastolic digital decisions as will be presently seen.

Pressure transducer 19, such as a National Semiconductor pressure transducer model LX1602G has been found in the present invention to provide an electrical signal output corresponding to the gage pressure level within cuff 12 and further provides an AC signal component Pa.c. superimposed on the gage pressure signal which is of a slowly varying d.c. characteristic. It has been found that the a.c. component, Pa.c., first becomes noticable approximately 20mm Hg above the patient's systolic pressure level. It has been found that the amplitude of the Pa.c. signal is preserved as the cuff pressure drops as low as 30 to 50mm Hg and below the diastolic pressure level. The Pa.c. signal is symbolically shown as a.c. coupled to an amplifier 34 via a capacitor 36 connected between the input of amplifier 34 and the output of transducer 19. The output of amplifier 34 is connected to the input of a lowpass filter 37. Filter 37 has characteristics which provide for passage of the relatively low frequency Pa.c. signal occuring at the heartbeat rate and excluding higher frequency and an undesired signal and noise components. The output of the filter 37 is connected to the input of decision means 38 such as a nonretriggerable one-shot. The one-shot may have a period of approximately 166 milliseconds. The output of means 38 is connected to a second input of digital logic block 32. The d.c. cuff pressure signal output from transducer 19 is connected to the input of d.c. amplifier 41 which has an output connected to the input of analog-to-digital converter 43. Converter 43 has an output connected to systolic and diastolic blood pressure displays 46 and 47 respectively which may be of conventional circuitry to provide an output indication of the respective pressure levels measured.

Digital logic block 32 has an output connected to an input of control logic block 48. Logic block 48 has an output connected to an additional input of analog-to-digital converter 43. As will be seen, logic block 48 in response to a digital logic signal from block 32 controls the operation of the converter 43 to provide the display outputs at the predetermined time when the respective pressure levels are determined. Digital logic block 32 additionally has heart rate start and heart rate stop outputs which are connected to control logic block 51. Block 51 has outputs connected to binary counters 53. Counters 53 have an input connected to the Pa.c. output of decision means 38 and further an output connected to the input of display counters 54 which in turn have an output connected to a digital indicator 56 to provide an indication of the measured heartbeat per minute rate.

Referring to FIG. 3, the detection circuitry within digital block 32 is shown. The detection means may comprise a "D" flip-flop 58 such as a single flip-flop of RCA Dual D flip-flop Model CD4013A having Q and $\overline{Q}$ outputs wherein the Q output provides $Q_{BP}$ signals as will be described below. The $+V_{cc}$ (logic high) is connected to the D input of the flip-flop 58 and the C or clock input is connected to the DP line from one-shot 38. The S input is connected to the common or ground terminal and the R or reset input is connected to the output of AND gate 61. Gate 61 has a KS input connected to the KS line which is connected to one-shot 31. A second input is connected via conventional logic within digital logic block 32 to provide an input signal 4DP corresponding to the fourth input DP signal. The circuitry to provide the delay or count of the four DP signal may be a conventional shift register providing an output to gate 61 after four successive DP signals have been received at the input of said shift register. Operation of detector means 58 will be discussed below in conjunction with the operation of the monitoring apparatus.

Turning to operation, the operator places the cuff on the patient and positions the microphone 26 over the brachial artery. Next the operator pumps up the cuff 12 approximately 20 to 30mm Hg above the patient's suspected systolic pressure level. Referring to FIG. 2, approximately 3 seconds after pumping stops a start pulse signal is generated at $t1$. Next a control signal 23 is provided to solenoid 21 to initiate a controlled pressure decay from cuff 12. At $t2$, a period of time after $t1$, the digital logic block 32 accepts Pa.c. and modifies said signal via the Pa.c. one-shot to provide a signal DP. Utilizing the present pressure transducer 19, DP signals may be detected at pressure levels above the systolic pressure, hence a delay of 3 DP pulses is introduced before enabling the microphone 26 signal KS at $t3$ to prevent spurious noise pulses. After the third DP signal at $t3$, the apparatus assumes a KS search mode.

Referring to FIG. 4, the operation of the detector means 58 of FIG. 3 may now be appreciated. As is well known in the measurement of heartbeat and the corresponding Korotkoff sound, the physiological relationship present is one of the heartbeat sound actually preceding the corresponding Korotkoff sound. The heartbeat sound signal output from the one-shot 38 provides a DP signal 64 and a corresponding KS signal 65 from one-shot 31. The combination of signals 67 and 68 generates the corresponding $Q_{BP}$ output signals from detector 58. It is to be noted that prior to $t3$ the detector 58 output is inhibited by the KS signal thereby adding noise immunity, in that the detector is only responsive to input signals within the expected signal range determined by the bandwidths of the KS signal channel and the DP signal channel. At $t3$, KS falls thus removing the inhibit signal to detector 58 and permitting the detector 58 to respond to a DP signal within a period of 270 milliseconds, that is the period of KS starting at $t3$. With the detector means 58 gate being open at the start of the range, that is, at $t3$ the detector looks for an output DP within the predetermined range. At $t4$, a DP signal is determined to occur coinciding within the expected range of the KS signal. Thus at $t4$ the $Q_{BP}$ 69 signal assumes a high level or holds an output level irrespective of input noise or other subsequent input signals. It is to be noted that this detection differs from that of a basic AND gate arrangement wherein the coincidence of two signals is always required to provide a coincidence output. The simple AND gate provides neither the noise immunity due to a predetermined range and further may have an erratic output if one input signal falls for a short period of time and then returns to the initial level thus providing a false signal output.

Referring again to FIG. 2, the DP and KS signals provide a $Q_{BP}$ signal at $t4$. The $Q_{BP}$ signal occurrence indicates that the Korotkoff sound was synchronously detected with a heartbeat induced a.c. change in blood pressure. At this point, the logic tentatively defines the $Q_{BP}$ signal at $t4$ as the tentative systolic point. However, verification is now required to further provide additional noise immunity and to ascertain that the tentative systolic point determination is a correct determination. Systolic pressure display 46 is caused to assume a display corresponding to the DC cuff pressure at the time $Q_{BP}$ was detected at $t4$. Similarly, at $t4$ the logic 32 is noted to assume a systolic confirmation mode wherein a predetermined number of $Q_{BP}$ signals must occur within a fixed period of time, such as three $Q_{BP}$ signals must occur within 2.5 seconds of each other.

Similarly at this time the DP signal and KS signal may also be used to provide in combination with suitable additional logic, the proper functioning of other monitoring apparatus test parameters. For example, the KS signal may be utilized in conjunction with additional gating circuitry to indicate whether the cuff pressure has been pumped high enough to provide an accurate reading. If an inadequate cuff pressure has been applied by the operator the KS signal will be immediately present at the 4DP time occurence and suitable indicating means may alert the operator that an inadequate cuff pressure has been utilized and that the test should be restarted at a higher cuff pressure.

If three $Q_{BP}$ signals occur within 2.5 seconds of each other, then at the leading edge $t6$ of the third $Q_{BP}$ pulse systolic is confirmed. Next the digital logic block 32 counts off two additional $Q_{BP}$ pulses and then assumes a diastolic search mode at $t7$. The sequence of systolic pulses continues until a gap of at least 2.5 seconds occurs in the $Q_{BP}$ train of pulses at which time the diastolic pressure level is considered to have occured. Concurrent with the systolic confirmation signal at $t6$ the diastolic display continues to update in response to the continuing pulses with a new update reading being provided with each $Q_{BP}$ pulse. When the diastolic pressure level was determined the display contents provide a valid diastolic pressure level.

The heart rate determining circuitry may be initiated after the third DP pulse, by initiation of a 15 second timer. For each DP pulse occuring within a 15 second interval 4 Pa.c. pulses are routed to the input of the heart rate display counter 54 and subsequently displayed on digital display 56.

Thus it is apparent that there has been provided an improved monitoring apparatus for blood pressure and heart rate which may be operated by unskilled personnel. Further there has been provided an improved monitoring apparatus for rapidly and accurately measuring the blood pressure and heart rate.

What is claimed is:

1. In a blood pressure and heart rate monitor: an inflatable cuff for controlled occlusion of a patient's artery, pressure responsive transducer means connected to the cuff for providing a first signal corresponding to the gage pressure in the cuff and a second signal corresponding to variations in the cuff pressure produced by expansion and contraction of the occluded artery due to the pumping action of the heart, means responsive to the first signal for indicating the patient's blood pressure, and means responsive to the second signal for indicating the patient's heart rate.

2. The monitor of claim 1 further including acoustic transducer means adapted to be positioned near the occluded artery for producing a signal corresponding to Korotkoff sounds in the artery, means responsive to the Korotkoff signal for conditioning the means for indicating blood pressure to indicate systolic and diastolic pressures, and means for correlating the Korotkoff signal with the heart rate signal from the pressure transducer to confirm the validity of the Korotkoff signal.

3. In a blood pressure monitor: an inflatable cuff for controlled occlusion of a patient's artery, pressure responsive transducer means connected to the cuff for providing a first signal corresponding to the gage pressure in the cuff and a second signal corresponding to variations in the cuff pressure produced by expansion and contraction of the occluded artery due to the pumping action of the heart, acoustic transducer means adapted to be positioned near the occluded artery for producing a signal corresponding to Korotkoff sounds in the artery, means for correlating the Korotkoff signal with the heart rate signal from the pressure transducer to verify the Korotkoff signal, and means responsive to the first signal from the pressure transducer and to the verified Korotkoff signal for indicating the patient's systolic and diastolic pressure levels.

4. The monitor of claim 3 further including means responsive to the second signal from the pressure transducer for indicating the patient's heart rate.

5. In a method for determining the blood pressure and heart rate of a subject, the steps of: occluding an artery of the subject with a pressurized cuff, effecting a controlled discharge of a pressurizing fluid from the cuff, monitoring the pressure in the cuff to provide a first signal corresponding to the gage pressure and a second signal corresponding to variations in the cuff pressure produced by expansion and contraction of the occluded artery due to the pumping action of the heart, processing the first signal to provide an indication of the subject's blood pressure, and processing the second signal to provide an indication of the subject's heart rate.

6. The method of claim 5 further including the steps of positioning an acoustic transducer near the artery to provide signals corresponding to the Korotkoff sounds in said artery, correlating the Korotkoff signals with the second signal to confirm the validity of the Korotkoff signals, and interpreting the blood pressure indication as either a systolic level or a diastolic level in accordance with the Korotkoff signals.

* * * * *